United States Patent [19]

Elam et al.

[11] 4,088,131
[45] May 9, 1978

[54] BREATHING ASSISTANCE DEVICE

[75] Inventors: James O. Elam, Chicago, Ill.; Hans Rudolph, Kansas City, Mo.

[73] Assignee: Jim E. Rand Training Systems, Inc., Chicago, Ill., a part interest; by said James Elam

[21] Appl. No.: 460,139

[22] Filed: Apr. 11, 1974

[51] Int. Cl.² .................................................. A61M 16/00
[52] U.S. Cl. ............................... 128/145.7; 128/145.8
[58] Field of Search ............... 128/145.7, 145.6, 145.5, 128/146.5, 146.4, 142.3, 202, 209, 210, 196, 197

[56] References Cited

U.S. PATENT DOCUMENTS

| 733,027 | 7/1903 | Goldan | 128/209 |
|---|---|---|---|
| 912,532 | 2/1909 | Brat | 128/209 |
| 955,121 | 4/1910 | Hollett | 128/196 |
| 1,176,886 | 3/1916 | Ermold | 128/209 |
| 3,262,446 | 7/1966 | Stoner | 128/146.5 |
| 3,473,529 | 10/1969 | Wallace | 128/145.7 |

FOREIGN PATENT DOCUMENTS

| 1,256,024 | 2/1961 | France | 128/145.7 |
|---|---|---|---|
| 16,236 of | 1893 | United Kingdom | 128/209 |
| 9,583 of | 1910 | United Kingdom | 128/209 |

Primary Examiner—Robert W. Michell
Assistant Examiner—Henry J. Recla
Attorney, Agent, or Firm—Curtis, Morris & Safford

[57] ABSTRACT

The lung inflation system specifically designed for use in the resuscitation of human beings. The system includes a manual compression bag which empties and refills through a single outlet opening. The compression bag is connected to a non-rebreathing valve which is specifically built, in accordance with the invention, so that the patient's lungs can be ventilated by means of the compression bag with pure oxygen, pure air, or a known mixture of both gases, as desired. The valve has a gas selector mechanism which makes it very easy for rescue personnel using the device to quickly select the mixture of gases which is needed. When available, oxygen from a pressurized oxygen source is supplied continuously to the valve device. The valve operates so that, when the compression bag is full, any excess oxygen being fed into the system is vented to the atmosphere through the same port as the one through which the breath exhaled by the patient passes. However, when the bag is compressed to inflate the patient's lungs, the exhaust port is closed so that the gases in the bag will flow only to the patient's lungs. When oxygen is not available the system operates to provide air for lung inflation.

11 Claims, 14 Drawing Figures

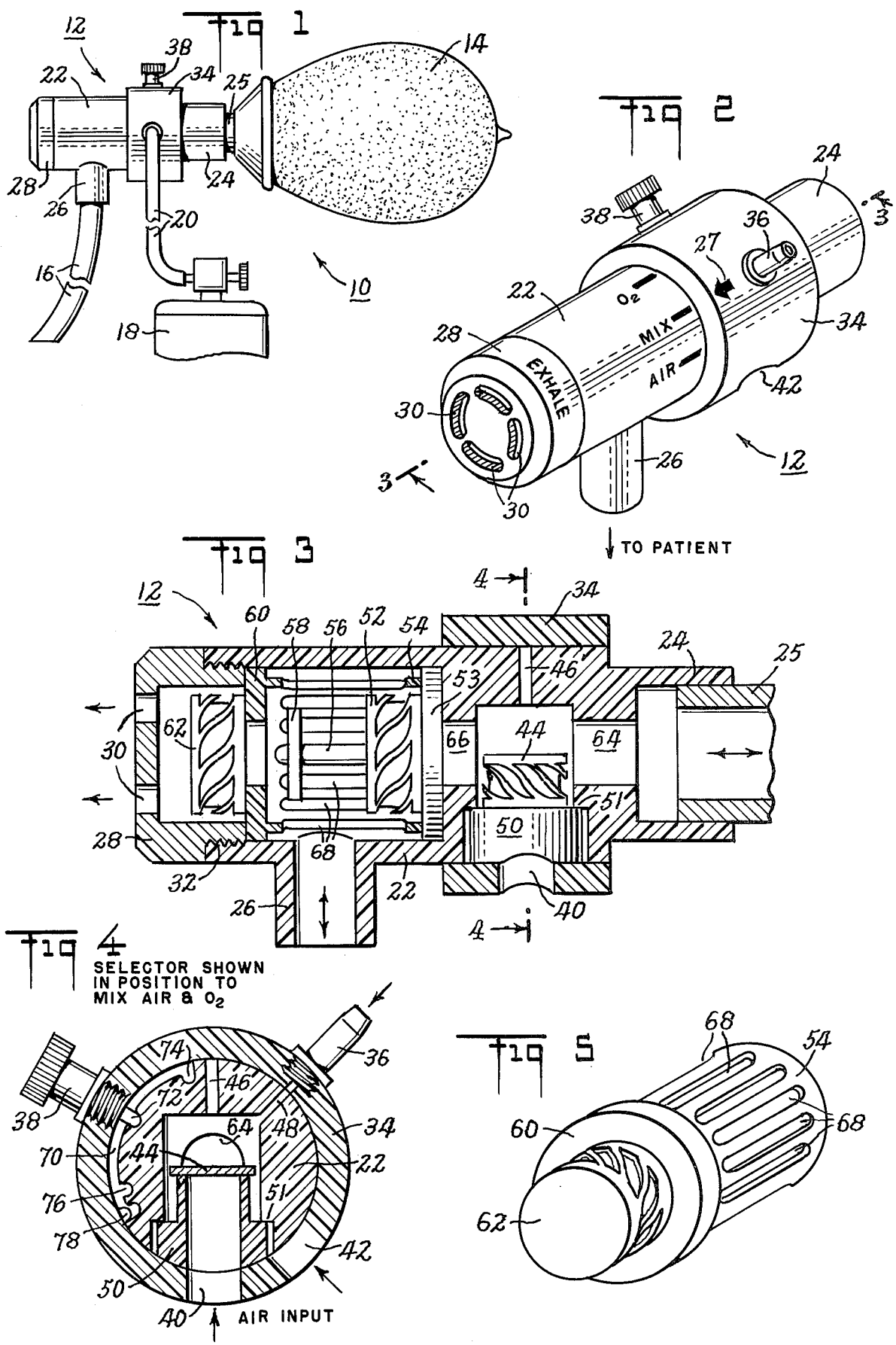

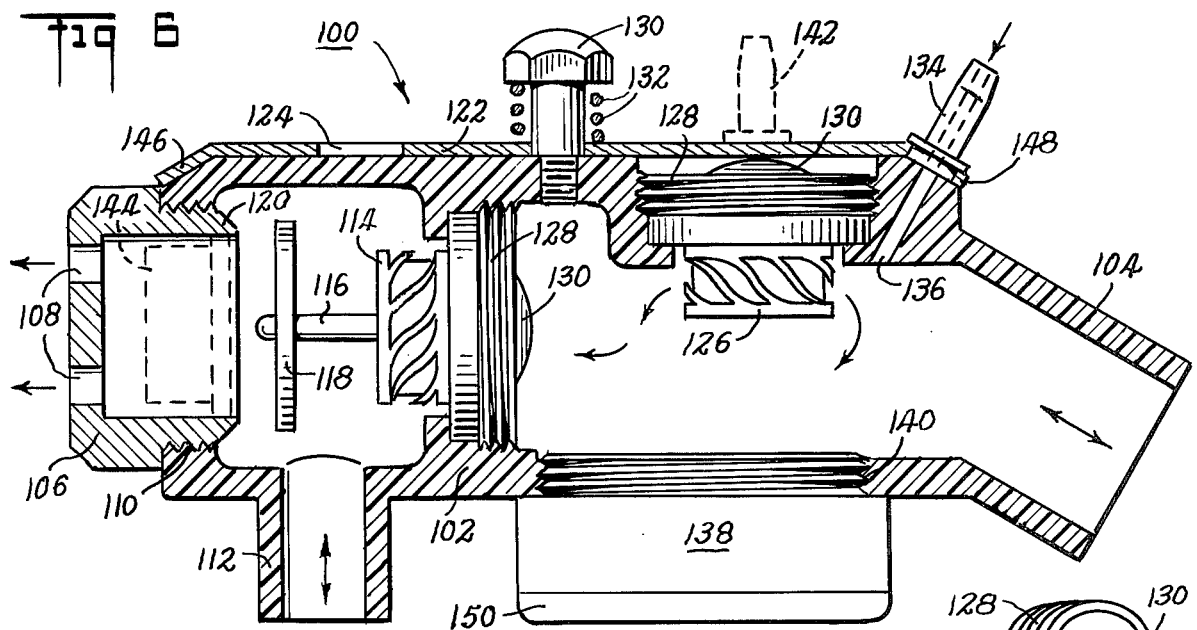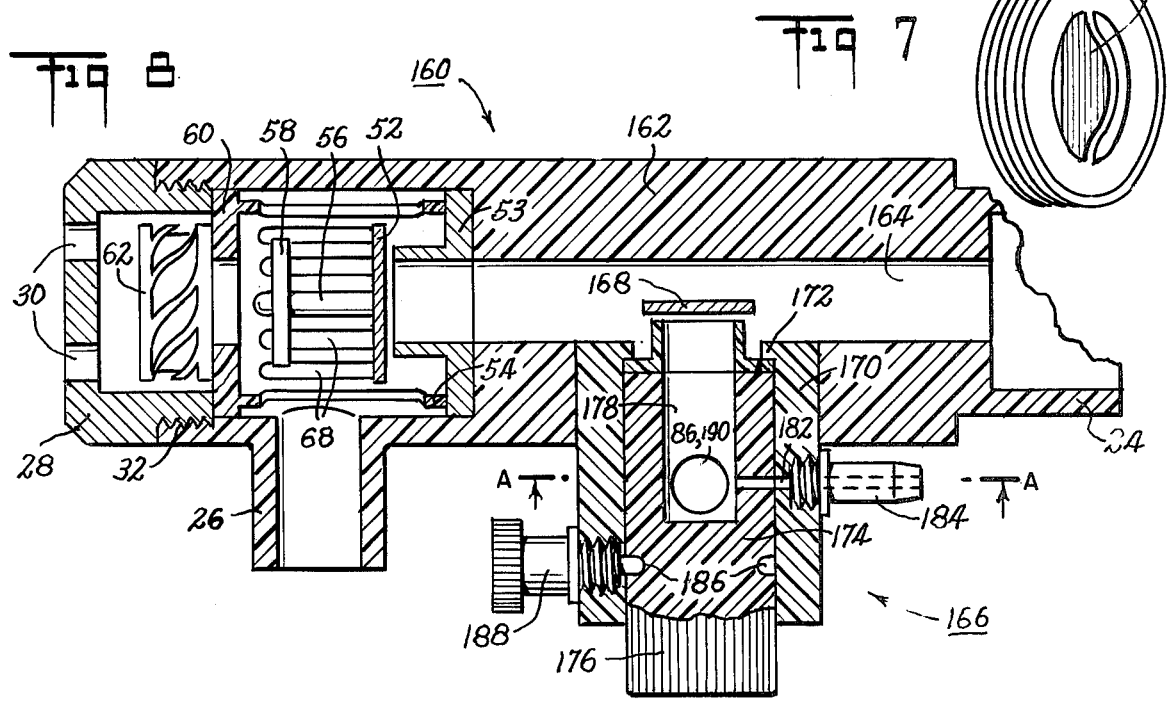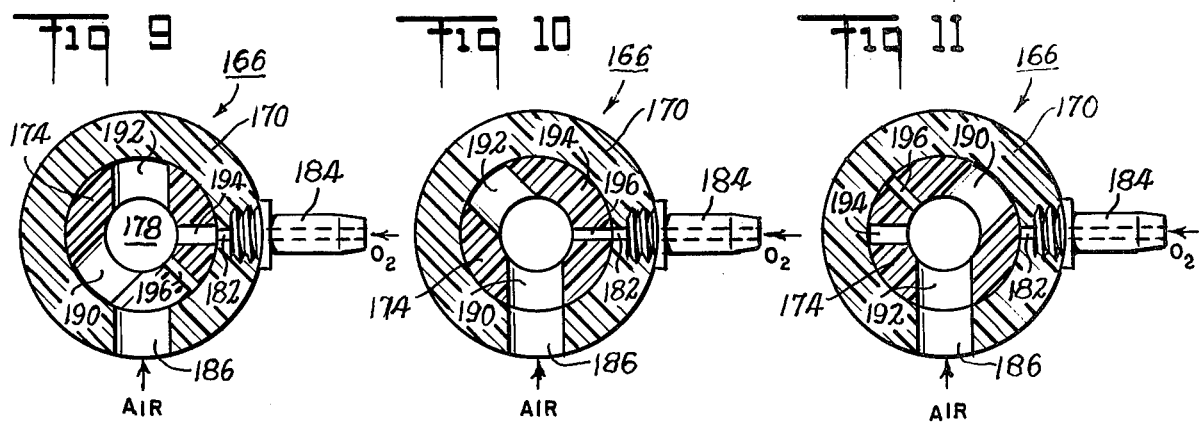

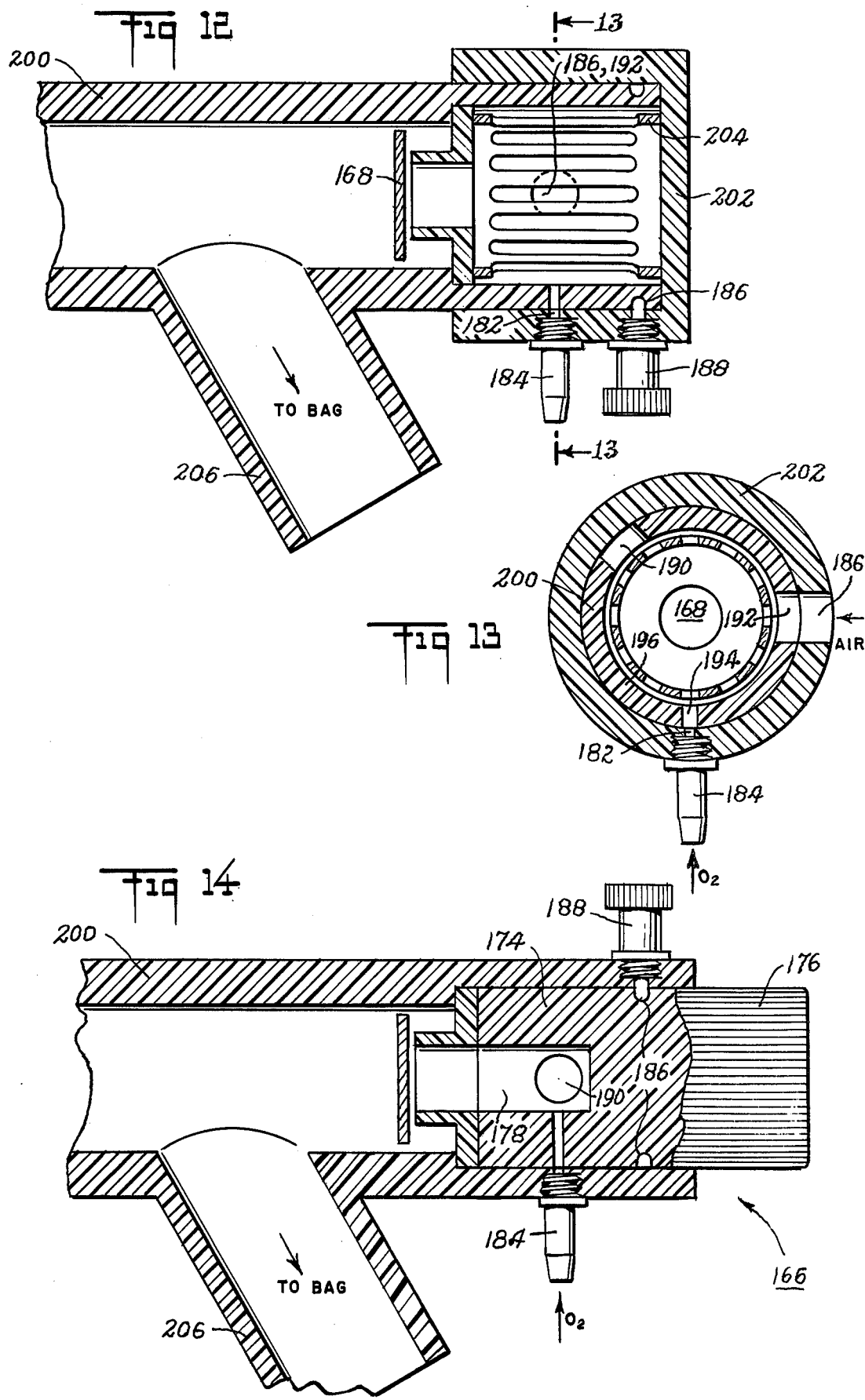

BREATHING ASSISTANCE DEVICE

This invention relates to devices and methods for providing artificial lung inflation with known oxygen mixtures for non-breathing human beings. More specifically, this invention relates to resuscitation devices and methods, and particularly to valves used in manual resuscitation equipment.

One type of resuscitation equipment commonly in use today has a manual self-refilling compression bag with a non-rebreathing valve for pumping air into a patient's lungs; i.e. to inflate the lungs of the patient. When it is desired to inflate the patient's lungs with oxygen, a connection is made to a source of pressurized oxygen such as an oxygen tank. However, the connection processes are slow, laborious and clumsy. Furthermore, some prior devices fail to elevate the patient's inspired oxygen level above 60%. The patient with arrested heart function often requires 100% oxygen for resuscitation.

Accordingly, it is an object of the present invention to provide a lung inflation system and method in which the oxygen concentration of gas being used to inflate the patient's lungs can be changed quickly and easily. It is another object of the invention to provide such a system and method in which excess oxygen is automatically vented to the atmosphere when not needed, so that the oxygen can be supplied continuously without causing the danger of building up pressure and rupturing the lungs of the patient. It is a further object of the invention to provide a valve device for performing the foregoing functions reliably and simply; one which is relatively simple in construction and easy to clean.

In accordance with the present invention, the foregoing objects are met by the provision of a lung inflation system including a manual compression bag which fills and empties through a single opening, a non-rebreathing valve device which continuously admits pressurized oxygen and makes it available to refill the compression bag, and which has means for selectively admitting air and/or oxygen. The valve assembly structure preferably has a movable selector member which blocks either an air inlet or an oxygen inlet, as desired, or opens both inlets simultaneously to mix the air and the oxygen in a desired ratio. The assembly has means for closing the exhaust port through which the patient's exhaled gas is passed when the bag is being compressed. However, the valve keeps the exhaust port open at all other times, including times when the compression bag is full and oxygen under pressure still is being supplied. The excess oxygen is vented to the atmosphere through the exhaust port so as not to close the exhaust port and rupture the lungs of the patient.

The foregoing and other objects and advantages of the invention will be set forth in or apparent from the following description and drawings.

In the drawings:

FIG. 1 is a partially-schematic elevation view of the lung inflation system and oxygen selection method of the present invention;

FIG. 2 is a perspective view of a preferred valve for use in the system shown in FIG. 1;

FIG. 3 is a cross-sectional view taken along line 3—3 of FIG. 2;

FIG. 4 is a cross-sectional view taken along line 4—4 of FIG. 3;

FIG. 5 is a perspective view of some of the components of the structure shown in FIGS. 2, 3 and 4;

FIG. 6 is a cross-sectional view of another embodiment of the valve device of the invention;

FIG. 7 is a perspective view of a component of the device shown in FIG. 6;

FIG. 8 is a cross-sectional view of another embodiment of the device;

FIGS. 9 through 11 are cross-sectional views, taken along line A—A of FIG. 8, showing the selector mechanism in its different positions;

FIG. 12 is a cross-sectional view of another embodiment of the valve device, with a portion of the device broken away;

FIG. 13 is a cross-sectional view of the selector taken along line 13—13 or FIG. 12; and FIG. 14 is a cross-sectional view of another embodiment of the device, with a portion of the device broken away.

The lung inflation system 10 shown in FIG. 1 includes a non-rebreathing valve device 12 and a manual compression bag 14 connected to the valve. The lung inflation system may be coupled to the patient by means of a well-fitting oro-nasal mask (not shown). Alternatively, a tube 16 which can be inserted in a patient's trachea for inflation of the lungs is connected to an outlet conduit 26 from the valve device 12. Oxygen is supplied under regulated pressure from a conventional oxygen tank 18 and flowmeter through a hose 20 to a connector 36 through which it is selectively admitted to the interior of the valve assembly 12 and the bag 14. The valve device 12 is "non-rebreathing" in that the gases exhaled by the patient cannot re-enter the bag and therefore are not readministered to the patient but are exhausted to the atmosphere.

In accordance with one aspect of the present invention, a rotatable selector device 34 is provided for admitting only pure oxygen to the valve device and compression bag.

Referring to FIGS. 2 through 5, and particularly to FIG. 3, the valve device 12 includes a body 22 of a generally cylindrical shape. The compression bag 14 is connected at the right end of 24 of the body 22. The compression bag is of a type which fills and empties through but a single port which is indicated at 25 in FIG. 3.

Air is admitted into the valve body 22 through an air inlet port 40 or 42 (see FIG. 4) and a check-valve 44. Oxygen is admitted into the valve body through the connector 36 and a port 46 or 48 (see FIG. 4). Gases flow to and from the patient through the conduit 26 in the left portion of the valve housing. Exhaled gases flow through exhaust ports 30 in the left end of the device by way of another check-valve 62. A third check-valve 52 is provided to admit gases from the compression bag and oxygen and air inlets, but to prevent exhaled gases from flowing back towards the compression bag.

Each of the three check-valves preferably is of a type shown in U.S. Pat. No. 3,063,461, whose disclosure hereby is incorporated herein by reference. However, other check-valves can be used if desired. The preferred check-valve includes a flexible rubber covering attached by springlike rubber legs to a support so that it will lift free of the opening in response to gas pressure in one direction, but will be pulled back towards its seat to close the opening in response to pressure in the opposite direction.

The valve 52 is of a special type, also shown in U.S. Pat. No. 3,063,461, which has a stem 56 projecting forwardly from the valve member with a disc 58 attached to it. The stem and disc are supported by a resilient structure (not shown) which biases the valve shut. When the valve 52 opens, the stem and disc 58 move to the left to block the port to exhaust valve 62 so as to prevent gases from exhausting to the atmosphere through the exhaust ports 30. By this means, gases from the compression bag all are directed to the patient during both lung inflation and natural inspiration. However, in accordance with the present invention, this special valve form is used for another purpose in addition to the purpose just described, namely, to vent excess oxygen to the atmosphere. This will be discussed in greater detail below.

The selector mechanism includes a ring 34 which fits closely around and forms a gas-tight seal with the cylindrical valve body 22. The connector 36 for receiving oxygen is secured to and extends from the ring 34, as does a detent knob 38. Referring particularly to FIGS. 2 and 4, the selector ring 34 has three different operating positions. In the first of these positions, the one shown in FIG. 4, a mixture of air and oxygen is admitted to the valve device. The setting of the selector to perform such mixing is indicated by means of an arrow 27 on the selector ring as is shown in FIG. 2. With the selector in this position, air enters the valve body through the inlet port 40 and the valve 44 adjacent the opening 25 of the compression bag. Oxygen enters through the inlet connector 36 and the conduit 48 which is aligned with the opening of the connector 36.

During the mode of operation in which pure oxygen is supplied, the detent knob 38 is pulled outwardly, pulling a pin 72 against a spring inside the detent mechanism, and the selector ring 34 is turned counter-clockwise (referring to FIG. 4) until the oxygen conduit 36 is aligned with the hole 46. With the selector in this position, the air inlet 40 as well as the inlet 42 will be blocked and air will not be permitted to enter the valve.

In order to operate the device so that only air is administered to the patient, the selector ring 34 is turned clockwise until the air inlet port 42 is aligned with the inlet to the check-valve 44. With the selector ring in this position, the oxygen inlet connector 36 is blocked so that oxygen cannot enter the valve body and only air can enter.

The valve body 22 has a circumferential groove 70 in which the pin 72 rides while the selector ring is being moved. The groove has three indentations in its bottom, one being the indentation in which the pin 72 is inserted as shown in FIG. 4, and the other two being indicated by reference numerals 74 and 76. The pin 72 engages one of these three notches to hold the selector ring in one of the three desired positions.

The valve body 22 also has a longitudinal groove 78 which is provided for the travel of the pin 72 when the selector ring 34 is pulled longitudinally to remove it from the valve body for cleaning. It should be noted that the pin 72 will not retract all the way out of the groove 70; it will retract only far enough to withdraw it from one of the indentations 74 or 76. Therefore, but for the groove 78, the selector ring could not be removed.

Still referring to FIG. 4, as well as to FIG. 3, the check-valve 44 is mounted on a base 50 of cylindrical configuration. The base 50 is mounted in a cylindrical bore in the housing and is seated against a flange 51.

The valves 52 and 62 are held in place by the following structure. Referring to FIG. 3, the exhaust ports 30 are formed in a cap 28 which is attached to the valve body 22 by means of screw threads 32. The valve 62 is mounted on an annular plate 60 which abuts against the left end of a cylinder 54 with a plurality of longitudinal slots 68. FIG. 5 is a perspective view of the valve 62, the plate 60, and the cylinder 54 in assembled relationship to one another.

Referring again to FIG. 3, the right end of the cylinder 54 abuts against another annular plate 53. The plate 53 abuts against an annular wall with a central gas flow passageway 66. The right end of the cap 28 abuts against the plate 60, thus pressing the plates 60 and 53 against the ends of the cylinder 54 and holding the assembly together.

OPERATION

Four basic steps are performed in the process of assisting the breathing of the patient. The first to be explained will be the ventilating step.

The lung inflation step is performed by manually compressing the bag 14 to force whatever gases it contains through the tube 16 (or a face mask) into the patient's lungs to ventilate them. During this phase of the operation, the check-valve 44 is closed to prevent gases from leaving the valve through either of the air input ports 40 or 42. The pressure provided by the compression bag is not enough, of course, to overcome the greater pressure at which oxygen is applied through inlet 46 or 48. Therefore, none of the gas from the compression bag flows outwardly through either of those ports. The valve 52 is open, thus allowing gas to flow from the bag through the passageways 64 and 66 in the valve body, through the valve 52, and through the outlet 26 to the patient. Furthermore, the opening of valve 52 pushes the stem 56 and the disc 58 all the way to the left and forces the disc 58 against the plate 60 to close the opening in the plate. This blocks the exhaust ports 30 and prevents gas from the compression bag from escaping through the exhaust ports.

During the next phase of operation, the operator releases the compression bag and its natural resilience tends to draw air inward through the inlet 25. During this phase of the operation, the valve 52 is closed, and the hole in plate 60 is open. The valve 44 is open to admit air into the valve (if air has been selected to be admitted) and oxygen continues to be supplied through port 46 or 48 (if oxygen has been selected). The compression bag then fills with the gas or gases thus being admitted into the valve body.

The third phase of operation occurs when the compression bag 14 is full, but before it is squeezed for the next ventilation of the patient's lungs. During this period of time, if oxygen is flowing into the valve, it continues to flow from the pressurized source. Thus, valve 52 opens. However, in accordance with one feature of the present invention, the oxygen is not allowed to enter in in sufficient quantity to completely open the valve 52, thus avoiding the closing of the exhaust ports 30 because the disc 58 does not move far enough to the left to cover the opening in the plate 60. Thus, the excess oxygen, instead of ventilating the patient through the outlet 26, is exhausted harmlessly to the atmosphere through the exhaust ports 30.

The fourth stage of operation, exhalation by the patient, actually takes place simultaneously with the second and third stages. Gases exhaled by the patient are free to travel through the valve 62 and out of the exhaust ports 30 during this phase of the operation. What is more, the exhaled gases will not flow back to the compression bag because of the check-valve 52. Even if the valve 52 is open to permit the exhausting of excess oxygen, the flowing oxygen will prevent the exhaled gases from being reintroduced into the compression bag.

The device shown in FIGS. 1 through 5 can be operated quickly and easily to change the mixture of gases being used to inflate the patient's lungs. What is more, this can be done simply and easily and without danger of hyperventilating the patient because of the unique feature permitting the exhausting of oxygen to the atmosphere, without the provision of extra structure for this purpose.

An alternative embodiment of the invention is shown in FIGS. 6 and 7. FIG. 6 shows only the valve structure 100 because the other parts of the system shown in FIG. 1 are the same. The squeeze-bag 14 is connected to a conduit 104, and the patient is connected to a conduit 112. The exhaust ports are shown at 108. The valve body 102 shown in FIG. 6 has a rectangular shape with a flat upper surface.

The selector mechanism includes a plate 122 which covers the upper surface of the body 102. When lifted, the plate is rotatable about a post 130 attached to the valve body in order to select the use either of pure oxygen or air to ventilate the patient. The plate can be lifted free of the valve body upwardly against a spring 132 which normally holds the plate tightly against the body 102. The plate 122 has a pair of angular side portions, 146 and 148, which mate with similarly-shaped portions of the valve body 122, thus, in effect, forming a detent structure to hold the plate in a position according to the type of operation selected.

The plate is shown in position for supplying pure oxygen. Oxygen is supplied through a connector 134 in the sloping portion 148 of the cover 122. The oxygen is admitted into the valve body 102 through an opening 136. When the plate 122 is rotated to its other position, a hole 124 in the plate 122 is above a check-valve 126 which will admit air into the valve from the ambient medium. Thus, selection between air or oxygen is made.

The exhaust ports 108 are in the end cap 106 which is attached to the valve body by means of threads 110, in a manner similar to the valve structure shown in FIGS. 2 through 5. A check-valve 114 of a construction identical to that of the check-valve 52 shown in FIG. 3 also is used. The valve 114 has a stem 116 with a disc 118 attached to it. The cap 106 has a sharp edge 120 against which the disc 118 abuts to close the exhaust ports 108 during ventilation of the patient.

Each of the check-valves 114 and 126 is held in place by means of a threaded nylon ring 128 (see FIG. 7) with a thumb plate 130 to be grasped to twist the ring for removal.

An additional check-valve 144 is shown in dashed outline adjacent the exhaust ports 108. It is optional (as is the corresponding valve 62 in FIG. 3) and is provided in order to enable the administration of oxygen to the patient after he has resumed breathing under his own power. Of course, with an appropriate setting of the selector mechanism, air can be admitted for the patient to breathe, if desired.

A relatively large access hole is provided at 140 in order to give access to the interior of the valve in order to replace the internal check-valves and clean the structure.

Advantageous use of this entry port is made by a canister 138 with a removable screw cap 150 which holds a spare check-valve for use as a replacement part. The canister 138 is threaded at one end for attachment to the valve body by means of similar threads at the edge of the hole 140.

An alternative position for the oxygen connector 134 is shown in dashed outline at 142. In this alternative structure, the hole 136 is eliminated because the oxygen enters through the same check-valve 126 that the air enters through. This simplifies the structure of the valve device.

FIGS. 8 through 10 of the drawings shown an embodiment of the valve which is the same as that shown in FIGS. 2 through 5, except for the parts which have different reference numerals. In essence, only the means for selecting the type of gas flow is different.

The new selector means 166 includes a tube 170 secured into the housing 162, and a rotatable insert 174 in the tube. The insert can be rotated to allow oxygen or air, or a mixture of oxygen and air, to flow into the housing 162 through a check-valve 168. The check-valve 168 is held in place by the insert 174 and a flange 172.

The outer end 176 of the insert 174 extends out of the tube 170 and has a serrated outer surface which makes it easy to grip and turn. In FIG. 8, the knob end 176 of the insert is shown in full lines to show the serrations, and the rest of the insert is shown in cross-section to show its internal passageways.

The insert 174 has a central bore 178, with several side ports shown in FIGS. 9 through 11. The tube 170 has a large air entry hole 186 and a smaller oxygen entry hole 182 in its side wall. The holes 186 and 182 are spaced from one another by 90°. The hole 182 communicates with an oxygen tube fitting 184 like the fitting 36 shown in FIGS. 1 through 5.

The fitting 184 is secured to the tube 170. This has the advantage that the fitting and the oxygen tube attached to it do not move when the selector knob 176 is turned, thus making use of the selector easier and less cumbersome than if the fitting were secured to the rotary selector part.

The insert 174 has a circumferential groove 186 with three indentations in the bottom to serve as detent holes. A spring-loaded detent 188 is mounted in the wall of the tube 170. The pin of the detent rides in the groove 186 to hold the insert 174 in the tube 170, and the pin fits into the groove 186 and is thrust by the detent spring into one of the holes in the groove bottom to hold the selector insert at one of its three operative positions. A longitudinal groove (not shown) of the same depth as groove 186 can be provided to facilitate removal of the insert for cleaning and for replacement of the valve 168. Alternatively, the detent 188 can be constructed so that its pin withdraws completely to allow the insert to be removed easily, thus avoiding the use of a longitudinal groove.

FIG. 9 shows the selector in a position giving pure oxygen flow. The insert has two oxygen flow holes 194 and 196, and two larger air flow holes 190 and 192. In the FIG. 9 position, hole 194 communicates with the oxygen flow passageway 182, but all of the other holes 190, 192 and 196 are blocked.

In FIG. 10, the selector has been turned to the mixture position, in which hole 196 passes oxygen and hole 190 passes air into the valve.

In FIG. 11, the selector has been turned to the pure air position, in which hole 192 passes air into the valve and all other holes 190, 194 and 196 are blocked.

It can be seen that the selector knob 176 needs to turn only through one-half revolution in order to cover its full range of selections. Therefore, the groove 186 need extend only half way around the circumference of the insert.

FIGS. 12 and 13 show another embodiment of the selector mechanism. The remainder of the valve is not shown, but it is identical to the left half of the valves shown in FIGS. 1 through 5 and 8 through 10.

The selector mechanism is at the right end of the valve body, and a tube 206 is secured to the body at an angle for attachment of the compression-bag. The general construction and operation of the valve is similar to that of FIGS. 8 through 11, except that the valve body 200 is used instead of the tube 170; a rotatable cap 202 replaces the insert 174; and a perforated cylinder 204 is used to hold the check-valve 168 in place. The oxygen connector 184 and detent 188 are secured to the cap 202.

The cap 202 is turned to select one of the three modes of gas supply. FIG. 13 illustrates the holes in the valve housing wall 200 and the cap 202. These holes are given the reference numerals of the holes shown in FIGS. 9 through 11 because they have the same relative angular relationships to one another, and function in the same way, except that the outside cap moves instead of the inner tube.

FIG. 14 shows another embodiment which locates the selector mechanism and bag outlet 206 in the same positions as in FIG. 12. The selector mechanism 166 is the same as that shown in FIGS. 8 through 11, except that the wall of the housing 200 replaces the tube 170.

The dimensional tolerances between the insert 174 and the inner wall of tube 170, and between the inner side wall of the cap 202 and the outer wall of the valve body 200 should be close so as to ensure a relatively gas-tight seal between the parts.

The materials which the valve devices are made are intended to be easily-cleanable plastic materials such as nylon. The valve devices easily can be disassembled for washing in a cleaning solution.

In all of the embodiments of the valve described above, the dimensions of the oxygen inlet opening and the distance of the disc 58 or 118 from its valve seat 60 or 120 should be selected so that at the pressures expected from the usual pressurized oxygen sources the flow will not be great enough to close the disc 58 or 118 against its seat, and yet the disc will seat under the greater flow from the compression-bag.

In a valve device constructed as shown in FIGS. 1 through 5, the oxygen inlets 46 and 48 were 2.7 millimeters and 2.6 millimeters in diameter. The usual range of pressures for the bottled oxygen used is from 2200 to 50 p.s.i.g. The distance between the disc 58 and seat 60 was 6 millimeters. The valve 52 was a model 1700 manufactured and sold by Hans Rudolph, Inc., Kansas City, Missouri.

The above description of the invention is intended to be illustrative and not limiting. Various changes or modifications in the embodiments described may occur to those skilled in the art and these can be made without departing from the spirit or scope of the invention.

We claim:

1. A lung inflation system, comprising, in combination, a manual compression-bag with a single inlet-outlet opening, a non-rebreathing valve connected to said opening, and gas control means for admitting to said opening air and oxygen from a pressurized source for filling said bag, and for exhausting to ambient oxygen in excess of the amount necessary to fill said bag, said gas control means including oxygen and air inlets, and a rotary member rotatable to a plurality of positions to selectively occlude said air and oxygen inlets, said valve including a cylindrical valve body, a transverse cylindrical extension therefrom, said air and oxygen inlets being located in said extension, and said rotary member being rotatably mounted with respect to said extension and having passageways communicating said inlets with the interior of said cylindrical valve body and being rotatable to bring said passageways selectively into alignment with said inlets.

2. A resuscitator valve structure comprising:
   a. a hollow body member having a flow passage therethrough, said hollow body member having an oxygen supply port and an inhalation port and an exhalation port each communicating with said flow passage;
   b. a tubular patient connection member mounted on said body member and communicating with the flow passage through said body member, said patient connection member being positioned between said inhalation port and said exhalation port, and between said oxygen supply port and said exhalation port;
   c. a gas storage means;
   d. means on said body member for connecting said gas storage means in continuous communicating relation with the flow passage through said body member, said storage means being adapted to selectively expel gas and to receive and store gas, said inhalation port and oxygen supply port being positioned between said means for connecting a gas storage and said patient connection member, said oxygen supply port being in continuous communication through said flow passage to said storage means;
   e. an inhalation valve unit having a seat member mounted in said inhalation port and a movable valve member normally urged into port closing engagement with said seat member, said valve member moving to port opening position in response to pressure on the seat side thereof whereby the valve unit is operative to close said inhalation port during gas flow from storage and to open said inhalation port in response to gas flow to storage;
   f. a flow control valve unit mounted in the flow passage through said body member having a first seat means between said patient connection member and said inhalation port and between said patient connection member and said oxygen supply port and a second seat means in said exhalation port, said flow passage being continuously open between said flow control valve unit and said storage means, said flow control valve unit having a movable valve means normally urged into passage closing engagement with said first seat means and open position with said second seat means whereby said flow control valve unit is operative to open the flow passage through said first seat means and close the flow passage through said second seat means in response to flow of gas into said body member from said storage means;

g. selector means including a member movably mounted on said body member, said movable member having first and second spaced openings therein, said movable member extending over said oxygen supply port and said inhalation port to close same and being movable on said body member to a plurality of positions in certain of which said first opening is aligned with said inhalation port to open same; and h. a fitting having a passageway therethrough mounted on said movable member of the selector means with said passageway communicating with said second opening and selectively movable to a position of alignment with said oxygen port to permit supplying oxygen to said storage means when said inhalation port is closed by said selector means movable member.

3. A resuscitator valve structure as set forth in claim 2 wherein said body member has a second oxygen supply port between said patient connection member and said means for connecting said gas storage means communicating with said flow passage through said body member, said plurality of openings in the selector means movable member includes a first aperture and a second aperture each respectively alignable with said inhalation port to open same, and the second aperture of said selector means member is positioned to be in alignment with said inhalation port and open same when said second opening and said fitting are aligned with said second oxygen supply port whereby said storage receives a mixture of air and oxygen.

4. A resuscitator valve structure as set forth in claim 2 wherein said exhalation port in said body member has an exhalation valve unit mounted therein and having a seat and a movable member normally urged into engagement therewith to close said exhalation port and prevent flow into the flow passage through said exhalation port and operative to open said exhalation port in response to gas flow into the flow passage from said patient connection member; said exhalation valve unit has means defining a second seat facing the flow passage through said body member; and said flow control valve unit has a second valve member engageable with said second seat of said exhalation valve unit to close said exhalation port when said movable valve member of said flow control valve unit is in open position for flow to said patient connection member.

5. A resuscitator valve structure as set forth in claim 2 wherein said movable member of the selector means to open and close said inhalation port comprises a collar rotatably mounted on said body member and said plurality of openings include an aperture therein selectively alignable with said inhalation port to open same; and said fitting being mounted on said collar and communicating with said opening is positioned to be alignable with said oxygen supply port when said aperture in said collar is out of alignment with said inhalation port whereby only oxygen enters said storage means.

6. A resuscitator valve structure as set forth in claim 5 wherein said body member has a second oxygen supply port between said patient connection member and said means for connecting said gas storage means communicating with said flow passage through said body member, said collar has a second aperture spaced from said first named aperture and selectively alignable with said inhalation port to open same, and the second aperture in said collar is positioned to be in alignment with said inhalation port and open same when said fitting is aligned with said second oxygen supply port whereby said storage receives a mixture of air and oxygen.

7. A resuscitator valve structure as set forth in claim 6 wherein said body member has a guideway in an exterior surface thereof, said guideway has an entrance portion and a selector portion, said selector portion of said guideway has a plurality of spaced recesses therein each corresponding to a selected position of said collar and said fitting thereon and said apertures therein, said collar has a detent movable along said guideway and resiliently urged into a respective recess in said guideway during rotation of said collar, and said detent has means thereon to permit manual removal of said from a respective recess to thereby permit rotation of said collar about said body member.

8. A respiratory apparatus and resuscitator valve structure therefor comprising a hollow body member having a flow passage therethrough and providing an intake chamber and a breathing chamber, said body member having an oxygen supply port and an inhalation port each communicating with the intake chamber, said body member having an exhalation port communicating with the breathing chamber, a tubular mouthpiece member having one end mounted on said body member and communicating with the breathing chamber, said mouthpiece member being positioned between said intake chamber and said exhalation port, a resilient storage container mounted on said body member and continuously communicating with the intake chamber, said container being collapsible and expandable whereby said container is adapted to expel gas when compressed and to receive and store gas during expansion, an inhalation valve unit having a seat member mounted in said inhalation port and having a portion thereof positioned in the intake chamber and a movable valve member normally urged into port closing engagement with said seat member, said valve member moving to port open position in response to pressure on the seat side thereof, the valve unit being operative to close said inhalation port during compression of said container and to open said inhalation port in response to expansion of said container, a flow control valve unit mounted in the flow passage and having a first seat means between said tubular mouthpiece member and said inhalation port and between said tubular mouthpiece member and said oxygen supply port and a second seat means in said exhalation port, said flow passage being continuously open between said flow control valve and said storage container with said oxygen supply port in continuous communication through said flow passage with said storage container, said flow control valve unit having a movable valve member normally urged into passage closing engagement with said first seat means and open position with said second seat means whereby said flow control valve unit is operative to open the flow passage through said first seat means and close the flow passage through said second seat means in response to flow of gas into said body member from said container, a selector means including a member movably mounted on said body member, said movable member having a plurality of spaced openings therein, said movable member extending over said oxygen supply port and said inhalation port closing same and being movable to a plurality of positions in certain of which respective openings align with said inhalation port to open same and in certain other positions to align with said oxygen supply port to open same, said plurality of openings in the selector member being arranged to close said oxygen supply port when said inhalation port is open to open said oxygen supply port when said inhalation port is closed, and a fitting mounted on said selector member and having communication therethrough by a respective one of said plurality openings and positioned to be alignable with said oxygen supply port when the other of said openings are out of alignment with said inhalation port, said fitting being connected to a source of oxygen under pressure.

9. An apparatus as set forth in claim 8 wherein said body member has a second oxygen supply port communicating with the intake chamber; said selector member comprises a collar rotatably mounted on said body member and said plurality of openings include a first aperture and a second aperture each respectively alignable with said inhalation port to open same, and the fitting on said selector member is position to be in alignment with said second oxygen supply port when said second aperture is in alignment with said inhalation port whereby said container receives a mixture of air and oxygen.

10. An apparatus as set forth in claim 9 wherein said exhalation port in said body member has an exhalation valve unit mounted therein and having a seat and a movable member normally urged into engagement therewith to close said exhalation port and prevent flow into the flow passage through said exhalation port and operative to open said exhalation port in response to gas flow into the breathing chamber from said mouthpiece member, said exhalation valve unit has means defining a second seat facing the breathing chamber and a passage communicating with said exhalation port, said flow control valve unit has a diaphragm for seating on said second seat of said exhalation valve unit to close said exhalation port when said flow control valve unit is open for flow to said mouthpiece member, and said flow control valve unit includes means for supporting said diaphragm and for guiding same during movement toward and away from said seat of said exhalation valve unit.

11. An apparatus as set forth in claim 10 wherein said body member has a guideway in an exterior surface thereof, said guideway has an entrance portion and a selector portion, said selector portion of said guideway has a plurality of spaced recesses therein each corresponding to a selected position of said collar and said fitting thereon and said apertures therein, said collar has a detent movable along said guideway and resiliently urged into a respective recess in said guideway during rotation of said collar, said detent has means thereon to permit manual removal of same from a respective recess to thereby permit rotation of said collar about said body member and movement of said detent into an other selected recess in said guideway, and said detent is movable along the entrance portion of said guideway to permit installation of said collar on said body member and removal of said collar from said body member.

* * * * *